US008901258B2

United States Patent
Caldararo et al.

(10) Patent No.: US 8,901,258 B2
(45) Date of Patent: Dec. 2, 2014

(54) COPOLYMERS FOR SOLAR CELLS BASED ON ACRIDONIC UNITS

(75) Inventors: Maria Caldararo, Trecate (IT); Andrea Pellegrino, Trecate (IT); Giuliana Schimperna, Novara (IT); Riccardo Po', Novara (IT)

(73) Assignee: ENI S.p.A., Rome (IT)

( * ) Notice: Subject to any disclaimer, the term of this patent is extended or adjusted under 35 U.S.C. 154(b) by 295 days.

(21) Appl. No.: 13/516,857

(22) PCT Filed: Dec. 15, 2010

(86) PCT No.: PCT/EP2010/007771
§ 371 (c)(1),
(2), (4) Date: Aug. 14, 2012

(87) PCT Pub. No.: WO2011/072876
PCT Pub. Date: Jun. 23, 2011

(65) Prior Publication Data
US 2013/0001474 A1    Jan. 3, 2013

(30) Foreign Application Priority Data

Dec. 18, 2009   (IT) .............................. MI2009A2232

(51) Int. Cl.
| | |
|---|---|
| C08G 61/12 | (2006.01) |
| C08G 73/06 | (2006.01) |
| C07D 409/14 | (2006.01) |
| C09D 11/10 | (2014.01) |
| H01L 51/00 | (2006.01) |
| H01L 51/42 | (2006.01) |

(52) U.S. Cl.
CPC ............ *C07D 409/14* (2013.01); *C08G 61/126* (2013.01); *H01L 51/0036* (2013.01); *C08G 2261/411* (2013.01); *C08G 2261/91* (2013.01); *H01L 51/0043* (2013.01); *C08G 61/123* (2013.01); *H01L 51/4253* (2013.01); *C08G 2261/3241* (2013.01); *C08G 2261/3246* (2013.01); *C08G 61/122* (2013.01); *Y02E 10/549* (2013.01)
USPC ........... 525/540; 525/242; 525/281; 525/423; 525/535

(58) Field of Classification Search
USPC .......................... 525/540, 242, 281, 423, 535
See application file for complete search history.

(56) References Cited

U.S. PATENT DOCUMENTS

| | | |
|---|---|---|
| 2004/0115473 A1 | 6/2004 | Burroughes et al. |
| 2008/0088228 A1 | 4/2008 | Noguchi et al. |

OTHER PUBLICATIONS

International Search Report issued Feb. 4, 2011 in PCT/EP2010/007771 Filed Dec. 15, 2010.

*Primary Examiner* — Duc Truong
(74) *Attorney, Agent, or Firm* — Oblon, Spivak, McClelland, Maier & Neustadt, L.L.P.

(57) ABSTRACT

The present invention relates to copolymers for solar cells based on acridonic units comprising: a monomeric unit (A) having general formula (I) wherein X is S or Se, Y is O, S or NR' and R, R', the same or different, are $C_4$-$C_{24}$ alkyl groups, aryl groups optionally substituted with other functional groups, acyl groups or thioacyl groups; at least one monomer unit (B) having general formula (II) wherein Z is O, S, Se or N—R", wherein R" is a $C_4$-$C_{24}$ alkyl group, an aryl group optionally substituted with other functional groups, an acyl group or thioacyl group, said monomeric unit (B) being connected to any position available of a hetero-aromatic side ring of the unit (A) through one of the two positions indicated by the dashed lines in general formula (II). Photovoltaic devices comprising said alternating π-conjugated polymers are also described.

18 Claims, No Drawings

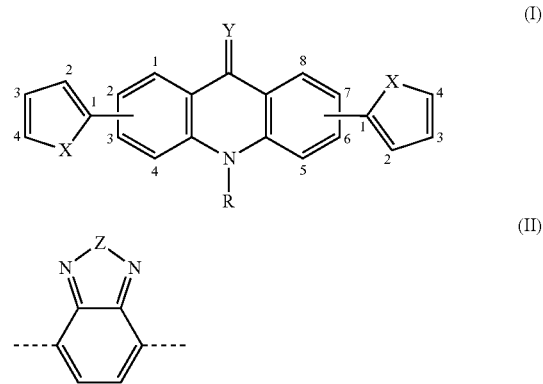

COPOLYMERS FOR SOLAR CELLS BASED ON ACRIDONIC UNITS

The present invention relates to copolymers for solar cells based on acridonic units.

In particular, the present invention relates to semiconductor copolymers having a conduction band with a low potential difference, suitable for the construction of photovoltaic devices active in the visible spectrum region.

Photovoltaic devices are devices capable of converting the energy of a light radiation into electric energy. At present, most photovoltaic devices which can be used for practical applications exploit the physico-chemical properties of photo-active materials of the inorganic type, in particular high-purity crystalline silicon. As a result of the high production costs of silicon, scientific research has been orienting its efforts towards the development of alternative organic materials having a conjugated, oligomeric or polymeric structure. Unlike high-purity crystalline silicon, in fact, conjugated organic materials are characterized by a relative synthesis facility, a low production cost, a reduced weight of the relative photovoltaic device, in addition to allowing the recycling of said polymer at the end of the life-cycle of the device in which it is used.

The functioning of organic and polymer photovoltaic cells is based on the combined use of an electron acceptor compound and an electron donor compound. In the state of the art, the most widely-used electron donor and acceptor compounds in devices described in scientific and patent literature are π-conjugated polymers belonging to the groups of poly-paraphenylene vinylenes and polythiophenes, and fullerene derivatives, respectively.

The basic conversion process of light into electric current in a polymer photovoltaic cell takes place through the following steps:
1. absorption of a photon on the part of the donor compound with the formation of an exciton, i.e. a pair of "electron-hole" charge carriers;
2. diffusion of the exciton in a region of the donor compound in which its dissociation can take place;
3. dissociation of the exciton in the two charge transporters (electron (−) and hole (+)) separated;
4. transporting of the charges thus formed to the cathode (electron, through the acceptor compound) and anode (hole, through the donor compound), with the generation of an electric current in the circuit of the device.

The photo-absorption process with the formation of the exciton and subsequent transfer of the electron to the acceptor compound consists in the transfer of an electron from the HOMO (Highest Occupied Molecular Orbital) to the LUMO (Lowest Unoccupied Molecular Orbital) of the donor and subsequently the transfer from this to the LUMO of the acceptor.

As the efficiency of an organic or polymer photovoltaic cell depends on the number of free electrons which are generated by dissociation of the excitons, one of the structural characteristics of the donor compounds which mostly influences said efficiency is the difference in energy existing between the HOMO and LUMO orbitals of the donor (so-called band-gap). In particular, the wave-length of the photons which the donor compound is capable of collecting and effectively converting into electric energy (so-called "photo harvesting" or "light-harvesting" process) depends on this difference.

Another important characteristic is the mobility of the electrons in the acceptor and electron holes in the donor, which determines the facility with which the electric charges, once photo-generated, reach the electrodes. This, in addition to being an intrinsic property of the molecules, is also strongly influenced by the morphology of the photoactive layer, which in turn depends on the reciprocal miscibility of the components and their solubility. Finally, a further fundamental characteristic is the resistance to thermo-oxidative and photo-oxidative degradation of the materials, which must be stable under the operating conditions of the device.

In order to obtain acceptable electric currents, the band-gap between HOMO and LUMO must not be too high, but at the same time, it must not be too low, as an excessively low gap would negatively affect the voltage obtained at the electrodes of the device.

In the simplest way of operating, the cells are produced by introducing a thin layer (about 100 nanometers) of a mixture of the acceptor and donor, between two electrodes. To obtain a layer of this type, a solution of the two components is prepared. A photoactive film is then created on the first electrode starting from the solution, using suitable deposition techniques such as "spin-coating", "spray-coating", "ink-jet printing", etc. Finally, the counter-electrode is deposited on the dried film.

The donor material most commonly used in the production of polymer solar cells is regioregular poly(3-hexylthiophene). This polymer has suitable electronic and optical characteristics (HOMO and LUMO orbital values; absorption coefficient), a good solubility in the solvents used for producing the cells and a reasonable mobility of the electronic gaps. The properties, however, are not optimum. The flow of photons of solar radiation which reaches the surface of the Earth, is in fact maximum for energy values of around 1.8 eV, (corresponding to radiations having a wavelength of about 700 nm). Due to the high band-gap values (generally higher than 2-3 eV) which characterize many of the polymeric materials currently known and used as donor compounds in photovoltaic devices. The light harvesting process of this spectral field is consequently not very efficient and only a fraction of the overall solar energy is converted into electric energy. As already mentioned, this is one of the main factors which cause low efficiencies in photovoltaic devices.

Among the polymers most widely-used as donor compounds, for example, the polymer MDMO-PPV (poly[2-methoxy-5-(3,7-dimethyloctyloxy)-1,4-phenylene]-alt-(vinylene)) and especially the polymer P3HT, used in combination with acceptor compounds based on fullerenes, are capable of obtaining maximum conversion efficiencies of solar radiation not higher than 5.4%.

In order to improve the yield of the light harvesting process and consequently the efficiency of photovoltaic devices, it is consequently fundamental to find new donor compounds capable of effectively capturing and converting the wavelengths of solar radiations having a lower energy, i.e. donor compounds characterized by lower band-gap values than those of the organic polymers typically used as donors.

Patent application US2008/0088228 relates to alternating conjugated copolymers comprising acridonic units variously substituted and units deriving from a series of different aromatic and heteroaromatic comonomers, which can be used in the preparation of photo-emitter diodes (OLED). The above document makes no mention of the use of these copolymers in the field of photovoltaic devices.

It is known that in identifying electroluminescent materials for the production of OLEDs, molecules characterized by tendentially reduced energy gaps below a certain threshold are not required, contrary to what occurs in the case of photovoltaic devices. The OLEDs must in fact be capable of emitting light radiation of many wavelengths, including white light. These wavelengths are generated by compounds having a wide energy gap spectrum, and each of them is optimized for a specific wavelength. In the case of photovoltaic devices, on the contrary, "low-gap" compounds must be found, in order to intercept the part of the spectrum with a higher intensity of solar radiation. Furthermore, whereas a material for OLEDs must have suitable properties for establishing efficient recombination processes of the hole-electron pair in order to obtain an optimum conversion of electrons to photons, in materials for photovoltaic devices, exactly the opposite conditions must prevail, as the recombination of the hole and electron recently generated would enter into competition with their separation and transportation to the electrodes, with a consequent unacceptable reduction in the generation efficiency of electric power.

A clear example of what is specified above is represented by polyfluorene, which is a material widely used in OLEDs, but totally unsuitable for the production of efficient polymer solar cells.

The Applicant has now found a particular group of photoconductor polymers with a low electronic gap comprising acridonic units, not specifically diffused in the art cited above, which is capable of overcoming the drawbacks indicated in the state of the art.

An object of the present invention therefore relates to a copolymer for solar cells based on acridonic units comprising:

a monomeric unit (A) having general formula (I)

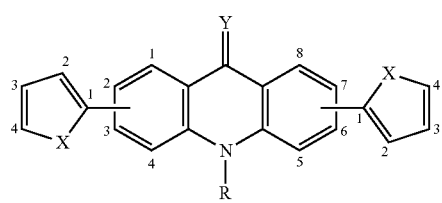

wherein
X is S or Se,
Y is O, S or NR'
and R, R', the same or different, are organic substituents having from 1 to 24 carbon atoms independently selected from alkyl groups, aryl groups optionally substituted, acyl or thioacyl groups;

at least one monomer unit (B) having general formula (II)

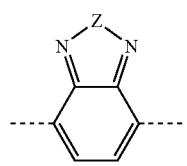

wherein Z is O, S, Se or N—R", wherein R" is an organic substituent having from 1 to 24 carbon atoms selected from alkyl groups, aryl groups optionally substituted, acyl or thioacyl groups, said monomeric unit (B) being connected to any position available of a hetero-aromatic side ring of the unit (A) through one of the two positions indicated by the dashed lines in general formula (II).

The unit (A) is an acridonic unit in which the benzene rings have substituent groups of the heteroaromatic type having an aromatic ring with 5 atoms.

In the unit (A), the two heteroaromatic side rings can be bound through any of their own positions 1, 2, 3, 4 to any of the positions 5, 6, 7, 8 of the benzene rings of the acridonic unit. The benzene rings of the acridonic unit are preferably substituted by heteroaromatic groups in positions 2 and 7 or 3 and 6.

Preferred R, R', R" substituents are those having from 4 to 20 carbon atoms. Examples of these substituents are the groups butyl, hexyl, octyl, decyl, dodecyl, tetradecyl, hexadecyl, octadecyl, eicosyl, 2-ethylhexyl, 2-ethyloctyl, 2-ethyldecyl, 2-ethyldodecyl, 4-butylhexyl, 4-butyloctyl, 4-butyldecyl, 4-butyldodecyl, 2-hexyloctyl, 2-hexyldecyl, 4-hexyldecyl, isopropyl, 1-ethylpropyl, 1-butylpentyl, 1-hexylheptyl, 1-octylnonyl, 1-dodecyltridecyl, 1-hexadecylheptadecyl, 1-octadecylnona-decyl, hexanoyl, octanoyl, decanoyl thiohexanoyl, thio-octanoyl, thiodecanoyl. The groups butyl, hexyl, octyl, decyl, dodecyl, 2-ethylhexyl, tetradecyl, hexadecyl, 4-hexyldecyl, 1-octylnonyl are preferred.

The copolymers, object of the present invention are alternating π-conjugated copolymers preferably having a structure of the repetitive base unit of the type $(A-B)_n$, wherein A and B have the meaning previously defined and n is an integer ranging from 1 to 1,000, preferably from 2 to 500.

Each unit A is bound to two B units, the same or different, except for when unit (A) or unit (B) represent terminal units of the polymeric chain. In this latter case, the terminal unit (A) or unit (B) are bound to one unit only, (B) or (A), respectively, and the remaining valence is saturated by a terminal substituent whose structure depends on the preparation method of the polymer and can be easily identified by an expert in the field. In most cases, this substituent is H or Br.

In order to increase the solubility of the copolymers according to the present invention in organic solvents, preferably the repetitive base unit (A-B) of the copolymer is substituted on at least one, preferably at least two of the positions of the molecular skeleton, with a group having a linear alkyl chain with at least 6, more preferably from 12 to 24, carbon atoms. These substituent groups can also coincide with one or more of the substituents R, R' or R" previously defined.

Alternating π-conjugated copolymers which are particularly preferred for the light harvesting properties shown, are those having the following repetitive base units: 3,7-dithienyl-N-hexyldecyl-acridone-2,1,3-benzo-thiadiazole (polymer 1), thiophene-N-hexyldecyl-acridone-thiophene-N-2-dodecyl-benzotriazole (polymer 2), 3,7-(3'-3"-hexyl)dithienyl-N-ethylhexyl-acridone-2,1,3-benzothia-diazole (polymer 3), 3,7-dithienyl-N-hexyldecyl-thioacridone-2,1,3-benzothiadiazol (polymer 4), 3,7-(3'-3"-hexyl)dithienyl-N-hexyldecyl-acridone-2,1,3-benzothia-diazole (polymer 5).

The copolymers, object of the present invention, can be synthesized by means of processes well-known to experts in the field. Processes for the preparation of copolymers based on the Stille and Suzuki reactions are particularly preferred.

The preparation process according to the Stille reaction is based on a reaction between an aryl dibromide and an organostannic compound in the presence of a Pd-based catalyst, which can be represented in general by the following scheme:

Stille Reaction

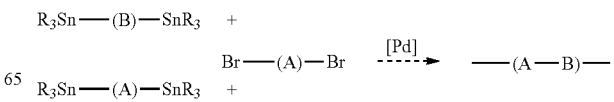

-continued

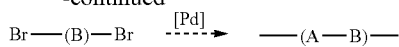

The preparation process according to the Suzuki reaction is based on a reaction between an aryl diboronic acid or a derivative thereof, for example an ester, and an aryl dibromide at room temperature in the presence of a catalyst based on a complex of Pd(0), which can be represented in general by the following scheme:

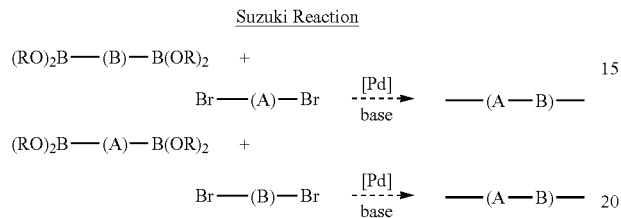

In the previous schemes, the units (A) and (B) of the copolymer are represented in brackets, to distinguish them from the boron atom B in the aryl diboronic acid used in the Suzuki reaction. It is up to the expert in the field to choose whether to use either one or the other of the reactions indicated for each of the two schemes.

The alternating copolymers based on acridonic units, object of the present invention, are characterized by band-gap values of around 2.0 eV or lower and can therefore be advantageously used as photoactive materials, in particular as electron-donor compounds in photovoltaic devices.

Thanks to the low band-gap value which characterizes them, these copolymers are capable of also collecting and effectively converting into electric energy, solar radiation with a higher wavelength, in particular that falling within the visible spectrum region. In this region, the donor compounds known and used in the state of the art have a limited efficacy.

A further object of the present invention therefore relates to a photovoltaic device comprising any of the copolymers of the present invention.

Another object of the present invention also relates to a solar cell comprising a photovoltaic device according to the present invention.

The copolymers, object of the present invention, can be used as electron-donor compounds for producing planar heterojunctions and bulk heterojunctions in photovoltaic devices, as solar cells.

The alternating conjugated copolymers can be used, for example, in the form of thin films (photoactive films) to produce planar heterojunctions coupled with films of electron-acceptor compounds. The two coupled films are put in contact between the two electrodes of a photovoltaic cell, according to techniques known in the art.

More preferably, the alternating conjugated copolymers, object of the present invention, are used as electron-donor compounds in bulk heterojunctions.

For this purpose, the photovoltaic cell is produced by introducing, between two electrodes, a thin layer (about 100 nanometers) of a mixture of one or more copolymers, object of the present invention, with at least one electron-donor compound.

In order to produce a layer of the kind described above, a solution of the two components is prepared in a suitable solvent, which, with the help of deposition techniques known to experts in the field (for example "spin-coating", "spray-coating", "ink-jet printing"), is distributed in the form of a thin photoactive film on a first electrode. Once dried, a counter-electrode is deposited on the film obtaining a photovoltaic device.

Electron-acceptor compounds which can be used in combination with the copolymers of the present invention, both in planar heterojunctions and bulk heterojunctions are electron-acceptor compounds known in the state of the art, for example compounds deriving from fullerene or derivatives of tetracarboxyperylenediimides or tetracarboxynaphthalenediimides. Photovoltaic devices comprising the heterojunctions which can be obtained with the copolymers, object of the present invention, have excellent light harvesting performances within the range of solar spectrum frequencies falling within the visible region, i.e. within the wavelength range of about 400 nm to about 700 nm.

As will be better illustrated in the following examples, the copolymers can be easily synthesized according to the process schemes previously illustrated.

EXAMPLES

Characterization of the Copolymers

Determination of the Molecular Weight

The molecular weight of the copolymers obtained according to the following examples was determined by means of GPC on a WATERS150C instrument, using HT5432 columns, with the eluent trichlorobenzene at 80° C.

The weight average molecular weight $M_w$ and the polydispersion index (PDI) are indicated, corresponding to the ratio $M_w/M_n$.

Determination of the Optical Band-Gap

The alternating π-conjugated polymers based on acridonic units according to the present invention were characterized by means of UV-Vis-NIR spectroscopy to determine the energy entity of the optical band-gap on thin film according to the following procedure.

The polymer is dissolved in toluene, chloroform, chlorobenzene, dichlorobenzene or another suitable solvent, obtaining a solution with a concentration of about 10 mg/ml, which is deposited by spin-coating on a quartz Suprasil. The thin film thus obtained is analyzed in transmission by means of a double-beam UV-Vis-NIR spectrophotometer and Perkin Elmer λ 950 double monochromator, within the range of 200-850 nm with a pass-through band of 2.0 nm, a scanning rate of 220 nm/min and step of 1 nm, using as reference an identical quartz Suprasil plate as such.

The band-gap is estimated from the diffuse reflectance spectra by measuring the absorption edge corresponding to the transition from the valence band (VB) to the conduction band (CB). For determining the edge, the intersection with the axis of the abscissa of the tangent line at the absorption band in the flexpoint was considered.

The flexpoint ($\lambda_F$, $y_F$) is determined on the basis of the coordinates of the minimum of the spectrum in first derivative, indicated with $\lambda'_{min}$ ed $y'_{min}$.

The equation of the tangent line at the UV-Vis spectrum in the flexpoint ($\lambda_F$, $y_F$) is:

$$y = y'_{min}\lambda + y_F - y'_{min}\lambda'_{min}$$

Finally, from the intersection condition with the axis of the abscissa ψ=0, the following is obtained:

$$\lambda_{EDGE} = (y'_{min}\lambda'_{min} - y_F)/y'_{min}$$

Therefore, by measuring the coordinates of the minimum of the spectrum in first derivative and the corresponding absorbance value $y_F$ from the UV-Vis spectrum, $\lambda_{EDGE}$ is obtained directly by substitution.

The corresponding energy is:

$$E_{EDGE} = h\nu_{EDGE} = hc/\lambda_{EDGE}$$

wherein $h = 6.626 \, 10^{-34}$ J s
$c = 2.998 \, 10^8$ m s$^{-1}$
i.e. $E_{EDGE} = 1.988 \, 10^{-16}$ J/$\lambda_{EDGE}$(nm).

Finally, remembering that 1 J=6.24 $10^{18}$ eV, the following is obtained:

$$E_{EDGE} = 1240 eV/\lambda_{EDGE}(nm)$$

Determination of HOMO and LUMO

The determination of the HOMO and LUMO values of the copolymers of the present invention is effected by means of the cyclic voltammetry (CV) technique. With this technique, it is possible to measure the values of the formation potentials of the cation radical and anion radical of the sample under examination. These values, when inserted in a specific equation, allow the HOMO and LUMO values of the copolymer to be obtained. The difference between LUMO and HOMO gives the electrochemical band-gap value.

The electrochemical band-gap values are generally higher than the optical band-gap value as, during the CV measurement, the neutral polymer is charged and undergoes conformational re-organization, with an increase in the energy gap, whereas the optical measurement does not lead to the formation of charged species.

The CV measurements are effected with an Autolab PGSTAT12 potentiameter (with GPES Ecochemie software) in a three-electrode cell. In the analyses effected, an Ag/AgCl electrode was used as reference electrode, a Platinum wire as counter-electrode and a vitreous graphite electrode as operating electrode. The sample is deposited as solution with a calibrated capillary onto the operating electrode, so as to form a polymeric film. The electrodes are immersed in an electrolytic solution 0.1 M of tetrabutylammonium tetrafluoroborate 95% in acetonitrile. The sample under examination is subjected to a triangular wave cyclic potential. Contemporaneously, in relation to the difference in potential applied, the current is monitored, which indicates oxidation reactions or a reduction in the species present.

The oxidation process corresponds to the removal of an electron from the HOMO, whereas the reduction cycle corresponds to the introduction of an electron in the LUMO. The formation potentials of the cation radical and anion radical are obtained from the value of the peak onset ($E_{onset}$), which is determined by molecules and/or chain segments with HOMO-LUMO levels closer to the edges of the bands. The electrochemical potentials to those relating to the electronic levels can be correlated if both refer to the gap. For this purpose, the potential of ferrocene is taken as reference in the gap, known in literature and equal to $-4.8$ eV. The intersolvential ferrocene/ferrocine (Fc/Fc$^+$) redox pair is selected as it has an electronic transfer energy independent of the operating solvent.

The general formula for calculating the energies of the HOMO-LUMO levels is therefore given by the following equation:

$$E(eV) = -4.8[E_{1/2 \, Ag/AgCl}(Fc/Fc^+) - E_{onset \, Ag/AgCl}(\text{polymer})]$$

wherein:
E=HOMO or LUMO depending on the value of $E_{onset}$ inserted.
$E_{1/2 \, Ag/AgCl}$=wave potential of the peak corresponding to the ferrocene/ferrocine redox pair measured under the same analysis conditions as the sample and with the same tern of electrodes used for the sample.

$E_{onset \, Ag/AgCl}$=onset potential measure for the polymer in the anodic area when the HOMO is to be calculated and in the cathodic area when the LUMO is to be calculated.

Method for Determining the Fluorescence

To determine the fluorescence of a thin film, a solution is prepared of about 10 mg/ml of polymer as such in toluene, chloroform, chlorobenzene, dichlorobenzene or any other suitable solvent. The solution is deposited on a quartz Suprasil by spin-coating obtaining a thin film. The sample thus obtained is analyzed with a Horiba Jobin-Yvon Fluorolog 3 spectrofluorometer exciting on the absorption maximums of the polymer. If there is emission, this is collected at 22° with respect to the incidence angle of the excitation beam. The fluorescence is always revealed at lower energies with respect to the absorption band with a lower energy of the polymer.

Method for Determining the Fluorescence Quenching

Fluorescence is a property which, when present in donor polymers for photovoltaic applications, is a consequence of the lack of non-radiative de-excitation paths, with a prolonging of the lifetime of the exciton until leading to the transfer of the charge from the donor to the acceptor, with the formation of a conduction band. To allow this to take place, however, the fluorescence must be quenched in the presence of the acceptor (for example, fullerene). The determination of the fluorescence quenching therefore represents evidence that the excitation energy deriving from the light absorption has been used for transferring the electron and producing electric energy.

In order to determine the quenching of the fluorescence of a thin film, a mixture is prepared in a solution containing about 10 mg/ml of the polymer and about 20 mg/ml of fullerene (6,6)phenylC$_{61}$butyric acid methylester (CAS160848-21-5; abbreviated hereafter as PCBM) in toluene, chloroform, chlorobenzene, dichlorobenzene or any other suitable solvent. The solution is deposited on a quartz Suprasil by spin-coating obtaining a thin film. The sample thus obtained is analyzed with a Horiba Jobin-Yvon Fluorolog 3 spectrofluorometer exciting, in correspondence with the absorption maximums of the copolymer, with the same inciding light power with which the fluorescence of the polymer as such was determined. If the fluorescence quenching on the part of PCBM is effective, the fluorescence of the polymer is substantially quenched.

Example 1

Synthesis of the Alternating Copolymer 3,7-dithienyl-N-hexyldecyl-acridone-2,1,3-benzothiadiazole The following products are charged, in an inert atmosphere, into a 250 ml two-necked flask equipped with a magnetic stirrer and reflux condenser:
764.8 mg (1.031 mmol) of 3,7-(2',2"-dibromo)-dithienyl-N-hexyldecyl-acridone,
405.70 mg (1.04 mmol) of 4,7-bis pinacolboronic-2,1,3-benzothiadiazole ester,
3 ml of anhydrous n-propanol,
1.5 ml of an aqueous solution 4 M of K$_2$CO$_3$,
100 ml of deaerated toluene.
The reaction mixture is heated to 70° C. for 15 minutes and, at this temperature,
122 mg (0.105 mmol) of Pd (0) tetrakis (triphenylphosphine) are added.
The reaction mixture is left at this temperature for 40 hours.

At the end of the period indicated, the mixture is concentrated to an eighth of the initial volume and then poured into 150 ml of methanol.

The precipitate obtained is filtered and suspended in a solution consisting of 100 ml of methanol and 100 ml of water. After 2 hours of vigorous stirring, the solid is filtered, re-dissolved in chloroform and then re-filtered on a porous septum.

The solution is concentrated to 15 ml and precipitated in 150 ml of methanol. The polymer thus obtained is filtered and left to dry in an oven at 55° C. for 3 days.

With this procedure 133.9 mg of a black solid were obtained.

The optical band-gap measured on a film of this copolymer is equal to 1.71 eV.

Other characteristics of the copolymer which were determined, are the following:

Energy of the HOMO=−5.17 eV,
Energy of the LUMO=−3.08 eV,
Molecular weight (Mw)=2,350 Da
PDI=1.549

The polymer has an emission band at 734 nm completely quenched when in a 1:2 weight mixture with PCBM.

Example 2

Alternating Copolymer thiophene-N-hexyldecyl-acridone-thiofene-N-2-dodecyl-benzotriazole The following products are charged, in an inert atmosphere, into a 250 ml two-necked flask equipped with a magnetic stirrer and reflux condenser:

71.7 mg (0.13 mmol) of 5,8-dimethyldiboronic-N-2-dodecyl-benzotriazole ester,
71.7 mg (0.19 mmol) of 5,8-diboronic-N-2-dodecyl-benzotriazole acid,
238.1 mg (0.32 mmol) of 3,7-(2',2"-dibromo)-bithiophene-N-hexyldecyl-acridone,
150 ml of deaerated toluene,
1 ml di anhydrous n-propanol,
0.5 ml of a 4 M solution of $K_2CO_3$.

The reaction mixture is heated to 70° C. for 15 minutes and, at this temperature, 50.0 mg (0.04 mmol) of Pd (0) tetrakis (triphenylphosphine) are added.

The reaction mixture is left at this temperature for 40 hours.

At the end of the period indicated, the mixture is concentrated to an eighth of the initial volume and then poured into 150 ml of methanol.

The precipitate obtained is filtered and suspended in a solution consisting of 100 ml of methanol and 100 ml of water. After 2 hours of vigorous stirring, the solid is filtered, re-dissolved in chloroform and then re-filtered on a porous septum.

The solution is concentrated to 15 ml and precipitated in 150 ml of methanol. The polymer thus obtained is filtered and left to dry in an oven at 55° C. for 3 days.

With this procedure 228.6 mg of a red solid were obtained.

The optical band-gap measured on a film of this copolymer is equal to 2.11 eV.

Other characteristics of the copolymer which were determined, are the following:

Energy of the HOMO=−5.30 eV,
Energy of the LUMO=−2.75 eV,
Molecular weight (Mw)=6,287 Da
PDI=2.263

The polymer has an emission band at 588 nm, 95% quenched when in a 1:2 weight mixture with PCBM.

Example 3

Alternating Copolymer 3,7-(3'-3"-hexyl)dithienyl-N-ethylhexyl-acridone-2,1,3-benzothiadiazole The following products are charged, in an inert atmosphere, into a 25 ml three-necked flask equipped with a magnetic stirrer and reflux condenser:

716.8 mg (0.898 mmol) of 3,7-(2',2"-dibromo)-(4'-4"-hexyl)dithienyl-N-ethylhexyl-acridone-2,1,3-benzothiadiazole,
350.3 mg (1.04 mmol) of 4,7-bis pinacolboronic-2,1,3-benzothiadiazole ester,
2 ml of anhydrous n-propanol,
1 ml of a 4 M solution of $K_2CO_3$,
10 ml distilled toluene.

The reaction mixture is heated to 70° C. for 15 minutes and, at this temperature, 15 mg (0.013 mmol) of Pd (0) tetrakis (triphenylphosphine) are added.

The reaction mixture is left at this temperature for 40 hours.

At the end of the period indicated, the mixture is subjected to distillation until the complete elimination of the solvent. The solid is re-dissolved in 20 ml of chloroform and is precipitated in 250 ml of methanol.

The precipitate obtained is filtered and suspended in a solution consisting of 100 ml of methanol and 100 ml of water. After 2 hours of vigorous stirring, the solid is filtered, re-dissolved in chloroform and then re-filtered on a porous septum.

The solution is concentrated to 15 ml and precipitated in 150 ml of methanol. The polymer thus obtained is filtered and left to dry in an oven at 55° C. for 3 days. The fraction insoluble in chloroform is dissolved in 20 ml of dichlorobenzene at 100° C., filtered on a porous septum and then precipitated in 200 ml of methanol. The solid thus obtained is filtered and dried in an oven at 55° C. for 3 days.

A total of 131.5 mg of a dark purple solid are obtained.

The optical band-gap measured on a film of this copolymer is equal to 1.89 eV.

Other characteristics of the copolymer which were determined, are the following:

Energy of the HOMO=−5.18 eV,
Energy of the LUMO=−3.21 eV,
Molecular weight (Mw)=60,321 Da
PDI=7.323

The polymer has an emission band at 670 nm completely quenched when in a 1:2 weight mixture with PCBM.

Example 4

Alternating Copolymer 3,7-dithienyl-N-hexyldecyl-thioacridone-2,1,3-benzothiadiazole The following products are charged, in an inert atmosphere, into a 25 ml three-necked flask equipped with a magnetic stirrer and reflux condenser:

377.6 mg (0.498 mmol) of 3,7-(2',2"-dibromo)-dithienyl-N-hexyldecyl-acridone,
194.5 mg (0.501 mmol) of 4,7-bis pinacolboronic-2,1,3-benzothiadiazole ester,
1 ml of anhydrous n-propanol,
0.5 ml of a 4 M aqueous solution of $K_2CO_3$,
5 ml of distilled toluene.

The reaction mixture is heated to 70° C. for 15 minutes and, at this temperature,
   6 mg (0.005 mmol) of Pd (0) tetrakis (triphenylphosphine) are added.
The reaction mixture is left at this temperature for 40 hours.
At the end of the period indicated, the mixture is subjected to distillation until the complete elimination of the solvent. The solid is re-dissolved in 20 ml of chloroform and is precipitated in 250 ml of methanol. The solid obtained is filtered and dried in an oven at 55° C. for 3 days.

With this procedure, a total of 341.1 mg of a reddish solid are obtained.

The optical band-gap measured on a film of this copolymer is equal to 1.71 eV.

Other characteristics of the copolymer which were determined, are the following:
   Energy of the HOMO=−5.13 eV,
   Energy of the LUMO=−3.21 eV.

Example 5

Alternating Copolymer 3,7-(3'-3"-hexyl)dithienyl-N-hexyldecyl-acridone-2,1,3-benzothiadiazole The following products are charged, in an inert atmosphere, into a 25 ml three-necked flask equipped with a magnetic stirrer and reflux condenser:
   1,053.3 mg (1.157 mmol) of 3,7-(2',2"-dibromo)-(4'-4"-hexyl)dithienyl-N-hexyldecyl-acridone-2,1,3-benzothiadiazole,
   449.4 mg (1.157 mmol) of 4,7-bis pinacolboronic-2,1,3-benzothiadiazole ester,
   3 ml of anhydrous n-propanol,
   1.5 ml of a 4 M solution of $K_2CO_3$,
   10 ml distilled toluene
   a few drops of aliquot.
The reaction mixture is heated to 70° C. for 15 minutes and, at this temperature,
   13 mg (0.011 mmol) of Pd (0) tetrakis (triphenylphosphine) are added.
The reaction mixture is left at this temperature for 40 hours.
At the end of the period indicated, the mixture is subjected to distillation until the complete elimination of the solvent. The solid is re-dissolved in 20 ml of chloroform and is precipitated in 250 ml of methanol. The solid obtained is filtered and suspended in a solution consisting of 100 ml of methanol and 100 ml of water. After 2 hours of vigorous stirring, the solid is filtered, re-dissolved in chloroform and then re-filtered on a porous septum 2.

The solution is concentrated to 15 ml and precipitated in 150 ml of methanol. The polymer thus obtained is filtered and left to dry in an oven at 55° C. for 3 days.

With this procedure, a total of 572.5 mg of a dark purple solid are obtained.

The optical band-gap measured on a film of this copolymer is equal to 1.94 eV.

Other characteristics of the copolymer which were determined, are the following:
   Energy of the HOMO=−5.31 eV,
   Energy of the LUMO=−3.06 eV,
   Molecular weight (Mw)=21,605 Da
   PDI=2.8
The polymer has an emission band at 670 nm completely quenched when in a 1:2 weight mixture with PCBM.

The invention claimed is:
1. A copolymer, comprising:
   a monomeric unit (A) of formula (I):

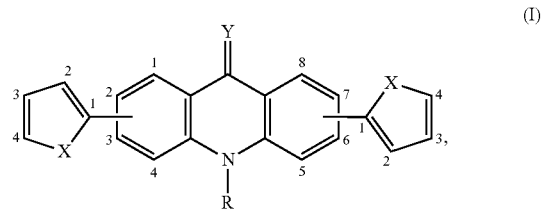

wherein
X is S or Se,
Y is O, S or NR' and
R and R' are organic substituents having from 1 to 24 carbon atoms independently selected from the group consisting of an alkyl group, an aryl group optionally substituted, and an acyl or thioacyl group; and
at least one monomer unit (B) of formula (II):

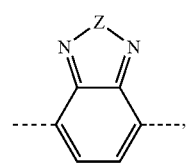

wherein Z is O, S, Se or N—R", and
wherein R" is an organic substituent having from 1 to 24 carbon atoms selected from the group consisting of an alkyl group, an aryl group optionally substituted, and an acyl or thioacyl group,
said at least one monomer unit (B) being connected to any position available of a hetero-aromatic side ring of the monomeric unit (A) through one of two positions indicated by dashed lines in formula (II).

2. The copolymer according to claim 1,
wherein X is S and Y is N—R', and
wherein R' is a substituent group having from 4 to 20 carbon atoms.

3. The copolymer according to claim 1,
wherein R, R', R" are independently selected from the group consisting of butyl, hexyl, octyl, decyl, dodecyl, tetradecyl, hexadecyl, octadecyl, eicosyl, 2-ethylhexyl, 2-ethyloctyl, 2-ethyldecyl, 2-ethyldodecyl, 4-butylhexyl, 4-butyloctyl, 4-butyldecyl, 4-butyldodecyl, 2-hexyloctyl, 2-hexyldecyl, 4-hexyldecyl, isopropyl, 1-ethylpropyl, 1-butylpentyl, 1-hexylheptyl, 1-octylnonyl, 1-dodecyltridecyl, 1-hexadecylheptadecyl, and 1-octadecylnona-decyl.

4. The copolymer according to claim 1,
wherein benzene rings of the monomeric unit (A) are substituted in positions 2 and 7 or 3 and 6 of formula (I).

5. The copolymer according to claim 1,
wherein a structure of repeating base unit of the copolymer is represented by formula $(A-B)_n$, and
wherein n is an integer ranging from 1 to 1,000.

6. The copolymer according to claim 5,
wherein the repeating base unit (A-B) is substituted on at least one position of a molecular skeleton of the repeating base unit (A-B), with a group having a linear alkyl chain with at least 6 carbon atoms.

7. The copolymer according to claim 5, wherein the repeating base unit is 3,7-dithienyl-N-hexyldecyl-acridone-2,1,3-benzothiadiazole.

8. The copolymer according to claim 5, wherein the repeating base unit is thiofene-N-esyldecyl-acridone-tiophene-N-2-dodecyl-benzotriazole.

9. The copolymer according to claim 5, wherein the repeating base unit is 3,7-(3'-3"-hexyl)dithienyl-N-ethylhexyl-acridone-2,1,3-benzothiadiazole.

10. The copolymer according to claim 5, wherein the repeating base unit is 3,7-dithienyl-N-hexyldecyl-thioacridone-2,1,3-benzothiadiazole.

11. The copolymer according to claim 5,
wherein the repeating base unit is 3,7-(3'-3"-hexyl)dithienyl-N-hexyldecyl-acridone-2,1,3-benzothiadiazole.

12. A planar or dispersed heterojunction, comprising the copolymer according to claim 1.

13. The planar or dispersed heterojunction according to claim 12,
wherein the planar or dispersed heterojunction comprises an electron-acceptor compound selected from the groups consisting of a fullerene, a tetracarboxyperylene diimide, and a tetracarboxynaphthalene diimide.

14. A photovoltaic device, comprising the copolymer according to claim 1.

15. A solar cell, comprising the photovoltaic device according to claim 14.

16. The copolymer according to claim 5,
wherein n is an integer ranging from 2 to 1000.

17. The copolymer according to claim 6,
wherein the repeating base unit (A-B) is substituted on at least two positions of the molecular skeleton, with the group having a linear alkyl chain with at least 6 carbon atoms.

18. The copolymer according to claim 6, wherein the repeating base unit (A-B) is substituted on the at least one position of the molecular skeleton, with a group having a linear alkyl chain with from 12 to 24 carbon atoms.

* * * * *